United States Patent [19]

Immel et al.

[11] 4,141,896
[45] Feb. 27, 1979

[54] PROCESS FOR THE PRODUCING ε-CAPROLACTAM FROM THE DISTILLATION OF CYCLOHEXANONE OXIME

[75] Inventors: Otto Immel, Krefeld, Fed. Rep. of Germany; André de Jager, Brasschaat, Belgium; Bernd-Ulrich Kaiser, Krefeld, Fed. Rep. of Germany; Hans-Helmut Schwarz, Krefeld, Fed. Rep. of Germany; Klaus Starke, Krefeld, Fed. Rep. of Germany

[73] Assignee: Bayer Aktiengesellschaft, Fed. Rep. of Germany

[21] Appl. No.: 832,008

[22] Filed: Sep. 9, 1977

[30] Foreign Application Priority Data

Sep. 15, 1976 [DE] Fed. Rep. of Germany ....... 2641381

[51] Int. Cl.$^2$ ............................................ C07D 201/04
[52] U.S. Cl. ................................................. 260/239.3 A
[58] Field of Search ................................. 260/239.3 A

[56] References Cited

U.S. PATENT DOCUMENTS

| 3,210,338 | 10/1965 | Huber et al. | 260/239.3 A |
| 3,586,668 | 6/1977 | Immel et al. | 260/239.3 A |
| 3,592,809 | 7/1971 | Immel et al. | 260/239.3 A |

Primary Examiner—Natalie Trousof
Assistant Examiner—Robert T. Bond
Attorney, Agent, or Firm—Connolly and Hutz

[57] ABSTRACT

A process for the production of ε-caprolactum from cyclohexanone oxime by rearrangement in the gaseous phase on a fluid-bed catalyst containing boron oxide, wherein residues from the distillation of cyclohexanone oxime are introduced into the reaction in liquid form, and wherein from 5 to 500 times their quantity of cyclohexanone oxime in vapor form and at least 50 times their quantity of inert gas are present during the reaction.

2 Claims, No Drawings

PROCESS FOR THE PRODUCING ε-CAPROLACTAM FROM THE DISTILLATION OF CYCLOHEXANONE OXIME

Cyclohexanone oxime cannot be distilled without the production of residues. Considerable quantities of distillation residues, consisting of dark-coloured, impure cyclohexanone oxime, are obtained. These residues cannot be further purified and are generally discarded.

One known process for the production of ε-caprolactam from cyclohexanone oxime is based on rearrangement in the gaseous phase in the presence of catalysts containing boron oxide. Fluidised bed reactors are generally used in large scale production. Gaseous cyclohexanone oxime is introduced into the fluidised catalyst bed together with an inert gas, such as nitrogen, and optionally steam and the oxime is rearranged into ε-caprolactam at temperatures of 250° to 400°C. Impure oxime or the oxime distillation residue cannot be used in this process because it cannot be converted into the gaseous phase.

The present invention provides a process for the production of ε-caprolactam from cyclohexanone oxime by rearrangement in the gaseous phase in the presence of a fluidised-bed catalyst containing boron oxide, wherein residues from the distillation of cyclohexanone oxime are introduced into the reaction in liquid form, and wherein from 5 to 500 times their quantity of cyclohexanone oxime in gaseous form and at least 50 times their quantity in inert gas are present during the reaction.

Providing these conditions are maintained, the cyclohexanone oxime distillation residues can be co-rearranged into ε-caprolactam without any danger of caking occurring in the reactor and without any reduction in the quality of the resulting ε-caprolactam.

The main difference between the cyclohexanone oxime residue and the pure cyclohexanone oxime is in colour. Whereas the residue is dark brown to black in colour, pure cyclohexanone oxime is colourless to pale yellow.

EXAMPLE 120 g/h parts by weight of oxime residue, obtained from the distillation of 1680 kg/h parts by weight of cyclohexanone oxime with 5% of water, were sprayed through a nozzle into the lower part of a fluidised bed reactor. The fluidised bed reactor contained 52,000 parts by weight of a catalyst containing boric acid which is kept in a state of fluidisation by 36,000 parts by weight of nitrogen and 5751 parts by weight of vaporised oxime. The temperature in the reactor was maintained at around 330° C.

The ratio of vaporised oxime to residual oxime was 48 whilst the ratio of inert gas to residual oxime was 300.

The reaction product leaving the reactor in the gaseous phase was condensed. The conversion, based on the cyclohexanone oxime used, amounted to 99.9% and the yield to 96%. The catalyst was partly run off at intervals and regenerated with air.

What we claim is:

1. A process for utilizing the dark brown to black residue which is obtained in the distillation recovery of pure cyclohexanone oxime which comprises introducing cyclohexanone oxime in the gaseous phase into a reaction zone in the presence of an inert gas and a boron oxide containing catalyst under conditions which rearrange said oxime and produce ε-caprolactam while simultaneously introducing said residue in liquid form into said rearrangement reaction zone, said reaction being carried out with a quantity of cyclohexanone oxime introduced in gaseous form which is 5 to 500 times the quantity of introduced liquid residue and with a quantity of inert gas which is at least 50 times the quantity of introduced liquid residue.

2. The process of claim 1 wherein the inert gas is nitrogen.